United States Patent
Mappes et al.

(10) Patent No.: US 9,176,051 B2
(45) Date of Patent: Nov. 3, 2015

(54) MICRO-OPTICAL ELEMENT, MICRO-OPTICAL ARRAY, AND OPTICAL SENSOR SYSTEM

(75) Inventors: Timo Mappes, Karlsruhe (DE); Heinz Kalt, Stutensee (DE); Tobias Grossmann, Darmstadt (DE); Torsten Beck, Stuttgart (DE); Tobias Wienhold, Karlsruhe (DE); Marko Brammer, Munich (DE)

(73) Assignee: KARLSRUHER INSTITUT FUER TECHNOLOGIE, Karlsruhe (DE)

( * ) Notice: Subject to any disclaimer, the term of this patent is extended or adjusted under 35 U.S.C. 154(b) by 0 days.

(21) Appl. No.: 14/129,554

(22) PCT Filed: Jun. 23, 2012

(86) PCT No.: PCT/EP2012/002657
§ 371 (c)(1),
(2), (4) Date: Feb. 10, 2014

(87) PCT Pub. No.: WO2013/000553
PCT Pub. Date: Jan. 3, 2013

(65) Prior Publication Data
US 2014/0226160 A1  Aug. 14, 2014

(30) Foreign Application Priority Data
Jun. 29, 2011 (DE) .......... 10 2011 107 360

(51) Int. Cl.
*H01S 3/083* (2006.01)
*G01N 21/27* (2006.01)
*G02B 26/00* (2006.01)
*G02B 5/10* (2006.01)
*H01S 3/08* (2006.01)
*G01N 21/77* (2006.01)

(52) U.S. Cl.
CPC *G01N 21/27* (2013.01); *G02B 5/10* (2013.01); *G02B 26/00* (2013.01); *H01S 3/08059* (2013.01); *G01N 2021/7789* (2013.01); *G01N 2201/0873* (2013.01)

(58) Field of Classification Search
CPC .......................... G01N 21/27; H01S 3/08059
USPC .................. 372/94; 385/30, 130; 359/291
See application file for complete search history.

(56) References Cited

U.S. PATENT DOCUMENTS 7,310,153 B2  12/2007  Kiesel et al.
7,387,892 B2   6/2008  Kiesel et al.
(Continued)

FOREIGN PATENT DOCUMENTS

EP   2287592 A1   2/2001

OTHER PUBLICATIONS

Armani, et al., "Heavy water detection using ultra-high-Q microactivities", Optics Letters, vol. 31, No. 12, Jun. 15, 2006, pp. 1896-1898.
(Continued)

*Primary Examiner* — Tuan Nguyen
(74) *Attorney, Agent, or Firm* — Leydig, Voit & Mayer, Ltd.

(57) ABSTRACT

A micro-optical element includes a resonator substrate, at least one microresonator includes a rotationally symmetrical body mounted on the resonator substrate, and a light-reflecting element including a ring-shaped mirror that surrounds the rotationally symmetrical body.

12 Claims, 5 Drawing Sheets

(56) References Cited

U.S. PATENT DOCUMENTS

| | | | |
|---|---|---|---|
| 7,388,706 B2* | 6/2008 | Miles | 359/291 |
| 7,667,200 B1* | 2/2010 | Watts et al. | 250/338.1 |
| 7,781,217 B2* | 8/2010 | Armani et al. | 436/57 |
| 7,951,299 B2* | 5/2011 | Hossein-Zadeh et al. | 216/2 |
| 8,358,884 B2* | 1/2013 | Grossmann et al. | 385/30 |

OTHER PUBLICATIONS

Vollmer, et al., "Whispering-gallery-mode biosensing: label-free detection down to single molecules", Nature Methods, vol. 5, No. 7, Jul. 2008, pp. 591-596.

Chronis, et al., "Total internal reflection-based biochip utilizing a polymer-filled cavity with a micromirror sidewall", Lab on a Chip, Royal Society of Chemistry, Bd. 4, Nr. 2, Jan. 1, 2004, pp. 125-130.

Kneissl, et al., "Current-injection spiral-shaped microactivity disk laser diodes with unidirectional emission", Applied Physics Letters vol. 84, Nr. 14, Apr. 5, 2004, pp. 2485-2486.

Knight, et al., "Phase-matched excitation of whispering-gallery-mode resonances by a fiber taper", Optics Letters, vol. 22, Nr. 15, Aug. 1, 1997, pp. 1129-1131.

Grossmann, et al., "High-Q conical polymeric microactivities", Applied Physics Letters 96, Jan. 4, 2010, pp. 013303-013303-3.

Armani, et al., "Label-Free, Single-Molecule Detection with Optical Microactivities", Sciencexpress, Jul. 5, 2007, pp. 1-10.

* cited by examiner

MICRO-OPTICAL ELEMENT, MICRO-OPTICAL ARRAY, AND OPTICAL SENSOR SYSTEM

CROSS REFERENCE TO RELATED APPLICATIONS

This application is a U.S. National Phase application under 35 U.S.C. §371 of International Application No. PCT/EP2012/002657, filed on Jun. 23, 2012, and claims benefit to German Patent Application No. DE 10 2011 107 360.8, filed Jun. 29, 2011. The International Application was published in German on Jan. 3, 2013, as WO 2013/000553 A1 under PCT Article 21(2).

FIELD

The invention relates to a micro-optical element comprising a resonator substrate on which at least one microresonator is mounted, said microresonator being designed in the form of a rotationally symmetrical body, to a micro-optical array and to an optical sensor system which comprises at least one micro-optical element or at least one micro-optical array.

BACKGROUND

In the fields of biology and medicine, there is a high degree of interest in sensors for selective, marker-free, high-sensitivity analysis of very small fluid quantities. One possibility for constructing such sensors is based on the use of optical cavities as microresonators, in particular in the form of toroids, goblets, discs, ellipsoids or spheres. At particular wavelengths $\lambda$, resonances form in the cavity. If molecules of an analyte become attached to the resonator surface, the effective radius R of the cavity increases due to a change in the refractive index n in the environment of the microresonator. A change in the radius R and the refractive index n brings about a change in the resonance wavelengths $\lambda_r$, as given by:

$$\frac{\Delta \lambda_r}{\lambda_r} = \frac{\Delta R}{R} + \frac{\Delta n}{n}.$$

According to F. Vollmer and S. Arnold in *Whispering-gallery-mode biosensing: label-free detection down to single molecules*, Nature Methods 5 (2008) 591-596, by analysing the spectrum, it is possible, from a shift in the wavelength of the resonance, to deduce attachment of molecules.

In order to be able to detect very small molecule quantities, microresonators with high quality factors are required. A. M. Armani, R. P. Kulkarni, S. E. Fraser, R. C. Flagan and K. J. Vahala describe in *Label-Free, Single-Molecule Detection with Optical Microcavities*, Science 317, pp. 783-86, 2007, label-free detection of individual molecules applied to the surface of a microresonator. A toroid made of silicon dioxide and mounted on a silicon foot on a silicon substrate was used as a microresonator.

T. Grossmann, M. Hauser, T. Beck, C. Gohn-Kreuz, M. Karl, H. Kalt, C. Vannahme, and T. Mappes describe in *High-Q conical polymeric microcavities*, Appl. Phys. Lett. 96 (2010) 013303, a method for producing microgoblet resonators made of polymethyl methacrylate (PMMA), which is distinguished by having a high degree of transparency in the visible spectral range, having a quality factor of above $10^6$.

In order to couple light into the cavity, evanescent coupling is used. J. Knight, G. Cheung, F. Jacques and T. Birks describe in *Phase-matched excitation of whispering-gallery-mode resonances by a fiber taper*, Opt. Lett. 22 (1997) 1129-1131, coupling into a microresonator by means of adiabatically thinned glass fibres. In order to obtain the most effective possible coupling, the diameter of the glass fibre must be thinned to values in the range of 0.1 μm to 3 μm. Due to the small diameter, the glass fibre becomes very fragile and handling thereof is made difficult. For the coupling between the fibre and the cavity, the distance must be set to values less than the wavelength of the irradiated light. This adjustment requires a high degree of positional accuracy and is possible only with micrometer tables and under controlled laboratory conditions. If the microresonator is used in a sensor for analysing a fluid, the adjustment is made more difficult by flow within the analyte.

EP 2287592 A1 discloses a micro-optical component for coupling laser light to microresonators, comprising at least one waveguide for laser light and at least two microresonators, each having the form of a rotationally symmetrical body arranged on a foot, preferably designed as a spheroid or a toroid, wherein the at least two microresonators are mounted on a first substrate which is provided with first side walls and the at least one waveguide is mounted on a second substrate which is provided with second side walls, such that the first side walls and the second side walls are rigidly connected to one another.

Resonance frequencies of the cavity create characteristic gaps in the transmitted spectrum in the waveguide, which are known as Lorentz curves. In order to resolve fine displacements of these resonances when molecules become attached to the structure of the resonator, the excitation must be carried out with a continuously tunable laser. The excitation frequency must follow the displacement of the resonance frequency. For this purpose, the whole spectral range being investigated is often continuously scanned with the excitation laser. The spectral analysis of the transmitted light must be carried out with a high resolution in order to detect the finest displacements, and for this purpose a spectrometer or a photodiode which is read out synchronously with the excitation laser is required.

In order to avoid complex adjustment of the glass fibre or waveguide, microresonators are coated or doped with an optical amplifier material, in particular a dye. If a doped cavity is pumped with an external laser having a dye-specific wavelength, a coherent emission can be stimulated. The spectrum emitted by the microresonator is characteristic of the geometry of the cavity and the active material being used. Due to the attachment of molecules from the analyte onto the resonator surface, apart from the resonance frequency, the emitted spectrum of the active microresonator is also displaced. This displacement serves as a sensor signal.

Microresonators doped with an active material emit light isotropically in the "resonator plane" along the whole periphery. Typically, the light emitted is collected with the end of a glass fibre or a lens. Due to the small aperture of the glass fibre, however, only a small part of the emitted light can be collected and detected. Since only a small part of the emitted light is scattered out of the plane at surface defects of the microresonator, it is also only a small intensity that can be collected with a lens positioned over the substrate. Using the above-mentioned detection methods, only a low signal-to-noise ratio is achievable.

In order to obtain directional emission, M. Kneissl, M. Teepe, N. Miyashita, N. M. Johnson, G. D. Chern and R. K. Chang describe in *Current-injection spiral-shaped microcavity disk laser diodes with unidirectional emission*, Appl. Phys. Lett. 84 (2004) 2485, a spiral-shaped resonator geometry which, in place of isotropic emission, enables directional emission. Due to the modified form of the microresonator, although the signal-to-noise ratio increases, the quality factor of the microresonator falls markedly, such that low molecule concentrations cannot be detected with this apparatus.

U.S. Pat. No. 7,387,892 B2 discloses a biosensor which is based on active rotationally symmetrical microresonators made from GaN/AlGaN. The emitted light is read out with integrated rows of photodiodes. As U.S. Pat. No. 7,310,153 B2 discloses, mounted on the row of photodiodes is a wedge-shaped thin-film filter which ensures that only particular wavelengths impinge on individual diode fields. Due to a resonance shift when an attachment from the analyte takes place, the intensity distribution on the photodiodes is altered. However, light emitted from the microresonator impinges on the detector from only a small angular segment, such that only a low signal-to-noise ratio is obtained. Due to the large distance between the microresonator and the detector of up to 1 cm, only a few microresonators can be placed on a substrate. Furthermore, a separate detector is provided for each microresonator, such that the complexity of the construction and connection technology is increased, since the detectors are manufactured on a separate substrate and are only subsequently mounted on the resonator substrate. Since the accuracy of detection depends on the number of photodiodes in a row, as the accuracy increases, the number of connections for reading out from the photodiode row also increases.

SUMMARY

In an embodiment, the present invention provides a micro-optical element a resonator substrate, at least one microresonator including a rotationally symmetrical body mounted on the resonator substrate, and a light-reflecting a ring-shaped mirror that surrounds the rotationally symmetrical body such that the rotationally summetrical body does not touch the ring-shaped mirror.

BRIEF DESCRIPTION OF THE DRAWINGS

The present invention will be described in even greater detail below based on the exemplary figures. The invention is not limited to the exemplary embodiments. All features described and/or illustrated herein can be used alone or combined in different combinations in embodiments of the invention. The features and advantages of various embodiments of the present invention will become apparent by reading the following detailed description with reference to the attached drawings which illustrate the following.

DETAILED DESCRIPTION

Figure 1:
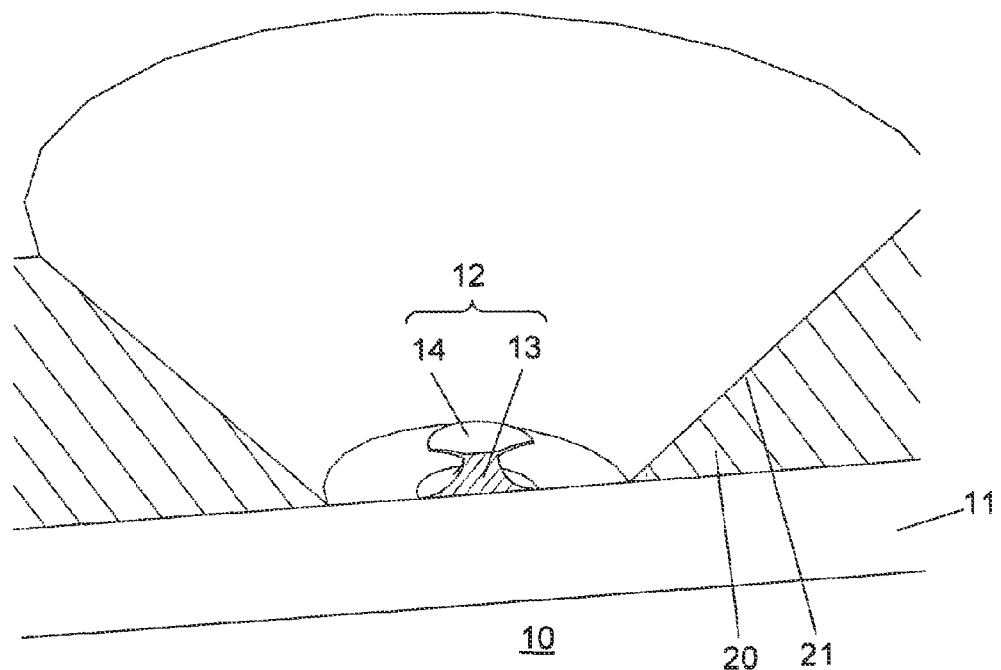
FIG. 1 shows a section through a micro-optical element.

An aspect of the present invention is to propose a micro-optical element, a micro-optical array and an optical sensor system in which at least one micro-optical element or at least one micro-optical array is mounted which do not have the above-mentioned disadvantages and limitations.

In particular, an integrated, portable, cost-effective optical sensor system is to be provided for robust and high-sensitivity detection of small quantities of molecules.

In an embodiment, the present invention provides a micro-optical element including a resonator substrate on which at least one, preferably one or two, microresonators are mounted, each having the form of a rotationally symmetrical body. If two microresonators are provided, these have the advantage that, given a suitable configuration, said microresonators emit only a single wavelength of coherent radiation. For the detection of molecules, preferably active rotationally symmetrical microresonators are used. Resonator geometries that are used are, in particular, annuli, discs, toroids, spheres or goblets.

Active materials that are used in the microresonators are
- in a first embodiment, the material of the at least one microresonator itself, preferably a semiconductor;
- in a second embodiment, the active material is introduced into the non-active material of the at least one microresonator as a dopant, preferably dye molecules which are introduced into a photostructurable material, preferably a polymer;
- in a third embodiment, as a layer applied onto the at least one microresonator made from a non-active material, preferably Alq3:DCM or dyes applied by means of auxiliary layers.

Suitable materials for dopants are rare earths, preferably erbium or ytterbium, nanocrystalline quantum dots, preferably made from CdSe/ZnS or dye molecules, in particular pyrromethene or xanthene (rhodamines).

For selective detection, only particular molecules may be allowed to couple to the at least one microresonator. For this purpose, the surface of the at least one microresonator is provided with a functionalisation which only allows the molecules being sought to attach to the microresonator. In the presence of a functionalised surface, displacement of the resonance frequency owing to attachment to the microresonator can therefore only be triggered by the molecules being sought.

In order to apply the functionalisation, preferably dip-pen nanolithography, electropipetting or chemical gas phase deposition is used. In a particular embodiment, the functionalising elements are directly introduced into the polymer matrix such that, subsequently, biological functionalisation is preferably enabled by means of "click chemistry".

In order to improve the signal-to-noise ratio of the detection signal, an increase in the intensity at the detector is desired. The at least one microresonator is therefore surrounded by a light-reflecting mirror, preferably a ring-shaped mirror which surrounds the rotationally symmetrical body of the microresonator. The shape of the light-reflecting mirror is preferably chosen such that the light emitted by the at least one microresonator can be guided away as effectively as possible.

In a particularly preferred embodiment, the angular profile of the mirror is matched to the radiation profile (emission profile) of the rotationally symmetrical body of the at least one microresonator such that the light emitted from the at least one microresonator is reflected perpendicularly or nearly perpendicularly to the substrate by the mirror.

The inner surface of the mirror is therefore preferably angled such that the horizontally radiated light is reflected as vertically as possible. The surface is preferably at an angle in the range of 30° to 70°, preferably 40° to 50°, in particular 45°±1° to the perpendicular.

In a preferred form, the mirror surface has a curvature of a paraboloid or a free form such that, in addition to the deflection of the emitted light, focusing also takes place. In a particularly preferred embodiment, the form of the ring is designed such that the light emitted is focused directly onto the detector, such that further focusing optics, for example lenses or optical elements integrated into the structure of the micro-optical element, are not required.

The internal diameter of the ring is selected such that said ring can be slid, with radial play, over the at least one microresonator. The diameter of the ring is in the range of 10 µm to 5000 µm, particularly in the range of 100 µm to 1000 µm. The height of the ring must be selected to be greater than the height of the resonator structure, and heights in the range of 1 µm to 500 µm, particularly in the range of 50 µm to 500 µm are preferable.

The mirror is preferably manufactured by replication techniques or etching methods from silicon, polymers or metallic materials. In a preferred variant, the manufacturing is carried out with polymers, in particular PMMA or a cyclic olefin copolymer (COC), using replication techniques, preferably by means of lithography, hot stamping, compression injection moulding or micromechanical machining.

The inner surface of the ring is preferably mirror-coated for high reflectivity. For this purpose, a thin layer of metal, preferably silver or aluminium, is applied by thermal vapour deposition or sputtering. Alternatively, other highly reflective coatings, in particular dielectric mirror coatings, are used. Preferably, this layer is applied only onto the inclined surface of the ring-shaped structure.

The mirror coating is preferably provided with a protective layer, in particular to protect against natural oxidation, which reduces the reflectivity. Magnesium fluoride $MgF_2$ in particular is suitable for this purpose. Alternatively, a layer of polytetrafluoroethylene (PTFE) or a similar fluoropolymer is applied.

The ring-shaped mirror is closed at the top, preferably with a cover through which the pumping light and the light emitted by the at least one microresonator is guided.

Integrated into or mounted in the structure of the cover in an advantageous embodiment are optical elements, preferably lenses, in particular Fresnel lenses, diffractive elements, in particular grating structures, and fluidic components, in particular microfluidic channels and fluidic inlets.

In a preferred variant, a lens structure is introduced into the cover, said lens structure focusing the pumping beam onto the at least one resonator structure and collecting the emitted light reflected at the mirror. A particularly preferred embodiment uses a Fresnel lens for this purpose.

In an alternative embodiment, the emitted light is evaluated horizontally. For this purpose, the cover is used as a waveguide. To achieve this, the emitted light reflected by the mirror is coupled into the waveguide via a structure stamped into, or applied onto, the cover, preferably a grating structure or a prism. The detector is arranged at the edge of the cover so that light guided in the cover impinges on the detector after coupling-out. In a particularly preferred embodiment, filtration of the emission of the at least one active resonator from the pumping light is achieved simply through the design of the grating structure.

Due to the resonator substrate, the ring-shaped structure and the cover, a closed volume is preferably formed round the at least one microresonator and is utilised, in a particularly preferred embodiment, as a fluid chamber. Through fluidic inlets and fluidic channels in the cover, the liquid or gaseous analyte can be fed into and pumped out of the fluid chamber.

The filling channels are preferably designed so that the analyte is fed into the channels by capillary force alone. In an alternative embodiment, the fluid is let into the fluid chamber through a dosing unit or a pump in the periphery.

The materials used for the cover and the lens should be transparent to the pumping light and the emission light and have low absorption levels. Preferred materials are biocompatible materials such as glass or polymers. Particularly preferred are materials which can be structured by means of replication methods, preferably by hot stamping, lithography, compression injection moulding or injection moulding.

In order to connect the resonator substrate, the ring-shaped structure and the cover, the ring-shaped structure is initially adjusted to the at least one microresonator and is then connected to the resonator substrate. The joining is preferably carried out by means of bonding, in particular through thermal or anodic bonding. Alternatively, an adhesive or an additionally applied adhesion promoting layer is used. Laser welding in order to connect the parts is also possible. Subsequently, the cover and the optical and fluidic structures integrated into the cover are adjusted to the ring-shaped structure and then connected using the aforementioned methods. In a particularly preferred variant, the resonator substrate, the ring-shaped structure and the cover are initially adjusted to one another and then connected to one another in a common joining step.

In a particularly preferred embodiment of the present invention, at least two, preferably a plurality of optical microresonators are structured as an array made from at least one microresonator per array element, on a common resonator substrate or on separate resonator substrates, and are surrounded by one light-reflecting mirror per array element.

The manufacturing of a plurality of microresonators as an array has the advantage that once an element of the array of at least one microresonator has already been used for detection, subsequently a change-over can be made to an as yet unused element of the array of at least one microresonator. If an unused element of the array of at least one microresonator is used for successive measurements, faulty measurements due to attachments on at least one microresonator from previous measurements are precluded. Once all the microresonators of one substrate have been used, it is advantageous to replace the whole array with a new array. By using replaceable arrays, biological or medical samples can also be investigated without complex cleaning and disinfection of the array.

Each array element made from at least one microresonator is surrounded by a light-reflecting mirror. The mirrors are preferably also manufactured as an array with the same number of elements as the microresonator array. Particularly preferably the mirrors of the array are manufactured simultaneously in parallel with the manufacturing method described, from a common workpiece. The manufacturing methods and materials described for the individual micro-optical element can also be used for the mirror layers and protective layers.

In a preferred embodiment, the array of ring-shaped structures is closed by a common cover. Each region of the cover which closes an individual ring-shaped structure of the array preferably contains one or more of the optical elements or fluidic structures described for the individual micro-optical element.

A further aspect of the present invention concerns an optical sensor system which comprises at least the following components:
- a device for efficient excitation of laser emissions from active microresonators, preferably a laser diode or a compact solid state laser, alternatively means for exciting electrically pumpable microresonators;
- a preferably replaceable micro-optical element or micro-optical array;
- a fluidic system for analyte infeed and flushing and a fluidic system for filling and flushing the fluid chamber; and
- a detector circuit for detecting a frequency shift in the light emitted from the at least one microresonator, in particular a device for spectral analysis, preferably based on an optical filter system which, in a particularly preferred embodiment, is based on a tunable optical filter having a steep cut-off for converting the frequency shift in the emission signal into an intensity change.

In a preferred embodiment, the optical sensor system also has one or more of the following components:
- a lens for the effective pumping of the at least one microresonator;
- a longpass filter to separate pumping light and emission from the at least one active microresonator;
- an amplifier circuit and electronics for signal evaluation;
- a device for temperature stabilisation of the at least one microresonator, preferably a Peltier element with control system, in particular with a temperature regulator and a temperature measuring system;
- fluidic elements, in particular pumps, valves for feeding in and pumping out the analyte and a reference and/or flushing solution.

In a compact optical sensor system, the active microresonators are preferably pumped with a laser diode which is markedly smaller and more economical than the solid state lasers which are normally used in the laboratory, although these are otherwise just as suitable for this purpose. In an alternative embodiment, means are provided which can be used to excite electrically pumpable microresonators.

If, in the optical sensor system, a micro-optical element or a micro-optical array is used, the cover of which does not have a lens for focusing the pumping light onto the active microresonator, in order to increase the pumping efficiency an additional collecting lens is preferably inserted between the pumping laser and the microresonator.

In order to address individual microresonators, the micro-optical element or the micro-optical array is displaced relative to the detector, filter and pumping source. For this purpose, in an advantageous embodiment, a one-dimensional or two-dimensional actuator mechanism is provided.

Variations in the ambient temperature have the effect that the temperature of the micro-optical element or array, and therefore the temperature of the at least one microresonator, vary during the measurement. As a consequence of an existing dependency of the refractive index on the temperature and due to thermally induced expansion, a temperature-dependent drift of the spectrum emitted by the at least one microresonator therefore takes place. This shift is overlaid by the frequency shift which arises due to the attachment of molecules to the resonator surface. Therefore, temperature stabilisation of the at least one microresonator is advantageous for unambiguous detection of the molecules. In a preferred embodiment, the micro-optical element or array is therefore temperature-stabilised from the rear thereof with a Peltier element during the measurement.

The present invention has, in particular, the following advantages.

The microresonators used are doped with an active material. Said microresonators therefore themselves function as a light source, such that no complex coupling-in of externally generated laser light into the microresonator is necessary; adjustment of a thinned glass fibre or of a waveguide to the microresonator with nanometer precision is not required.

Pumping of the active material of the microresonators by means of an external laser does not require high-precision positioning. If the diameter of the pumping beam is selected to be greater than the diameter of the at least one microresonator, merely coarse positioning is sufficient.

Provided on the micro-optical element and/or micro-optical array by the mirror and the cover is a fluidic structure which conveys the analyte in a targeted manner to the at least one microresonator. An additional delimitation of the fluidic channel is not needed.

With the optical sensor system, an integrated, portable device is provided for robust and high-sensitivity detection of the smallest quantities of molecules.

The present micro-optical element and/or array can also be used for efficient light gathering for applications in the field of quantum optics. A preferred example is the manufacturing of single photon sources.

The manufacturing of these light sources is carried out similarly to the production of the active microresonators. For this purpose, low concentrations of quantum dots or other stable emitters are introduced into or applied onto the microresonators. The emitting behaviour of the emitters under optical stimulation is altered by the presence of a microresonator surrounding said emitter, such that the emitters do not emit the photons isotropically, but in the direction of the optical modes. The emitted light is collected highly efficiently by the mirror of the micro-optical element and/or array, such that the photons are available for further quantum optical applications, in particular for intercept-proof quantum encryption purposes.

FIG. 1 shows a three-dimensional view of a section through a micro-optical element (10) according to the invention. Mounted on a resonator substrate (11) is an active microresonator (12) which consists of a microgoblet made of polymethyl methacrylate (PMMA) as the rotationally symmetrical body (14), which is arranged on a foot (13) and to which the dye pyrromethene is added as an active material. Arranged round the microresonator (12) is a mirror (20) which has a ring-shaped mirror structure with a conical profile, wherein the microresonator (12) is arranged in the centre of the conical ring-shaped structure. Applied onto the conical surface of the ring-shaped structure (20) is a reflective coating (21) which consists of silver and is encapsulated by a protective layer of magnesium fluoride ($MgF_2$) for protection of said coating against oxidation.

For the manufacturing of the microresonators (12), an approximately 1 μm-thick layer of PMMA was applied to a silicon wafer by rotation coating. The structuring of the microresonators was carried out by means of electron beam lithography or DUV (Deep Ultraviolet) lithography. For sensor applications, resonator diameters in the range of 10 μm to 300 μm, in particular from 10 μm to 150 μm were used. The structures were then undercut by isotropic etching of the silicon with xenon difluoride $XeF_2$. As a result of a subsequent thermal melting-on process, the microresonators formed a goblet structure with low surface roughness.

As the active material, the dye pyrromethene was directly dissolved in the polymer matrix of the rotationally symmetrical body (14). Alternatively, organic semiconductors can be vapour deposited on the rotationally symmetrical body (14) or dyes can be applied onto the rotationally symmetrical body (14) by dip-pen nanolithography or click chemistry. In order to protect the active materials against oxidation or detachment, a thin protective layer of parylene was applied.

Figure 2:
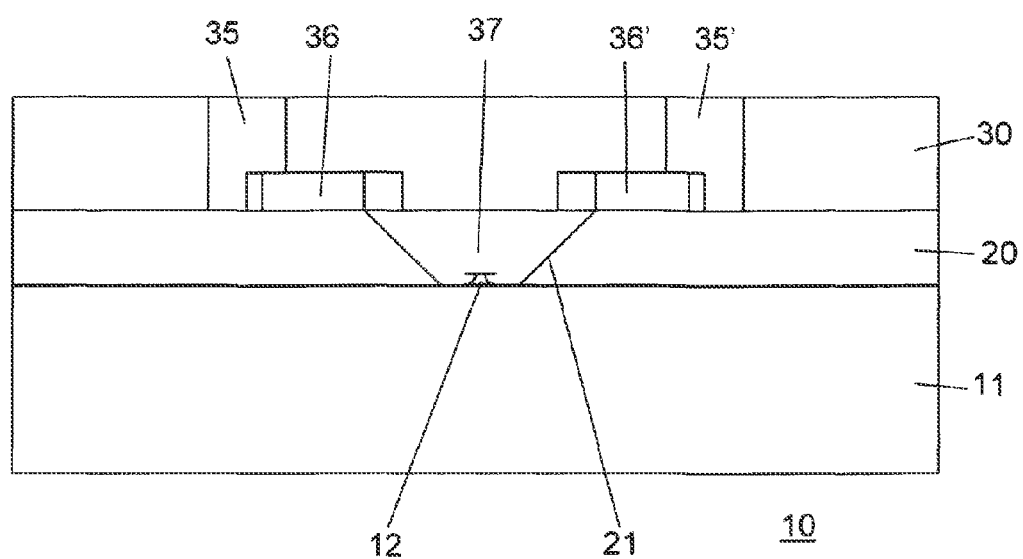
FIG. 2 shows a cross-section through a micro-optical element with a cover.

FIG. 2 shows a cross-section through a micro-optical element (10) according to the invention. In addition to the components shown in FIG. 1, an optically transparent cover (30) with fluidic inlets (35, 35') and fluidic channels (36, 36') is applied to the ring-shaped mirror (20). The resonator substrate (11), the ring-shaped mirror (20) and the cover (30) together constitute a closed fluid chamber (37) into which an analyte can be introduced via the fluidic inlets (35, 35') and fluidic channels (36, 36').

Applied to the ring-shaped structure in this preferred embodiment is an optically transparent cover (30) made of polymethyl methacrylate (PMMA) or cyclic olefin copolymer (COC). The structures of the fluidic inlets (35, 35') and of the fluidic channels (36, 36') were introduced into the cover (30) by hot stamping, injection moulding or compression injection moulding. The resonator substrate (11), the ring-shaped mirror (20) and the cover (30), following adjustment thereof to one another, were connected to one another by a common thermal bonding step, so as to form the closed fluid chamber (37).

Figure 3:
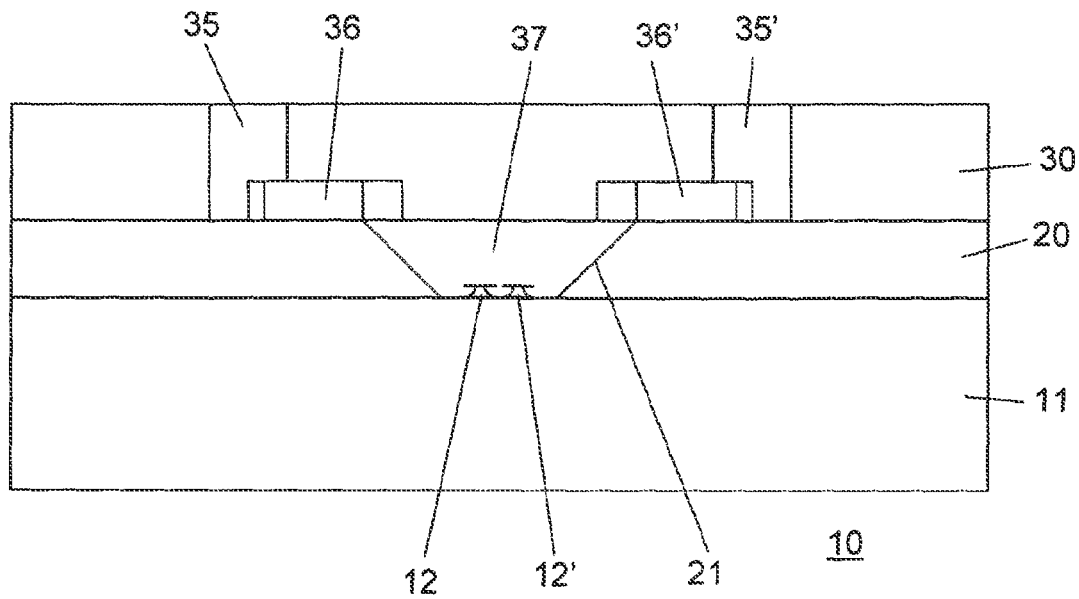
FIG. 3 shows a cross-section through a micro-optical element with two microresonators and a cover.

FIG. 3 shows a cross-section through a further embodiment of the micro-optical element (10). As distinct from FIG. 2, provided in the centre of the ring-shaped mirror (20) are two microresonators (12, 12'), the horizontally emitted light therefrom being reflected by the light-reflecting mirror layer (21) on the ring-shaped structure (20) perpendicularly to the resonator substrate (11).

Figure 4:
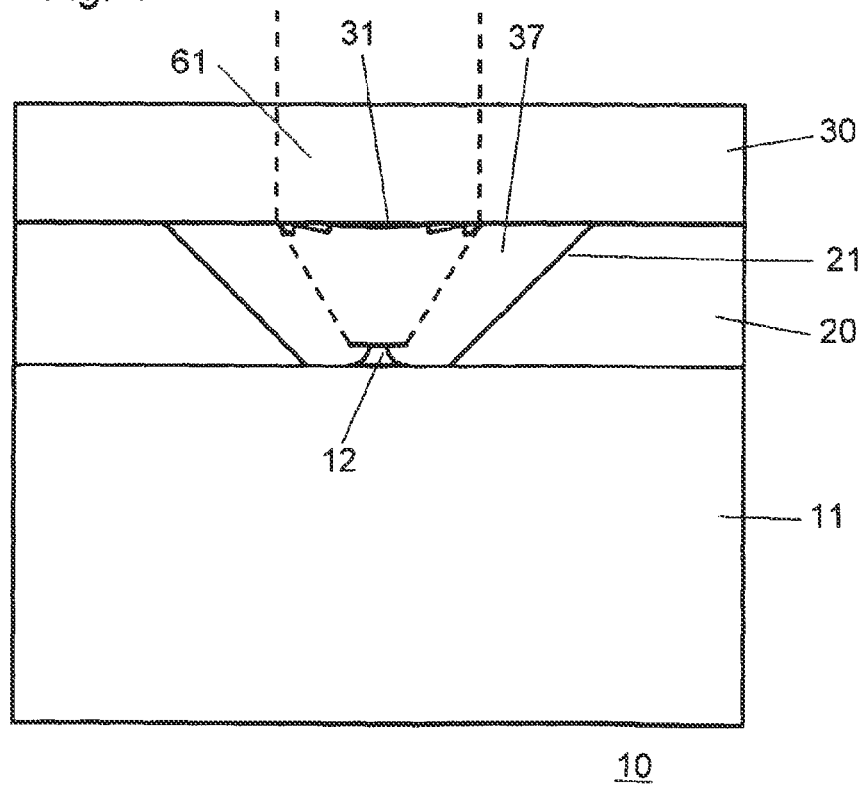
FIG. 4 shows a cross-section through a micro-optical element with a cover which is provided with a lens for point focusing of an incident pumping beam (illustrated)

According to FIG. 4, introduced into the cover (30) of a further embodiment of the micro-optical element (10) is a Fresnel lens (31) for point focusing of a pumping beam (61) onto the structure of the rotationally symmetrical body (14) of the microresonator (12). As a consequence of the focusing, as compared with excitation without a lens, more efficient excitation of the emission from the rotationally symmetrical body (14) of the microresonator (12) is achieved, with the result that the threshold for the emission of coherent radiation is lowered. The structure of the Fresnel lens (31) for point focusing of the pumping beam (61) was introduced into the cover (30) by hot stamping, injection moulding or compression injection moulding. Alternatively, it can be applied by thermal bonding or gluing onto the structure of the cover (30).

Figure 5:
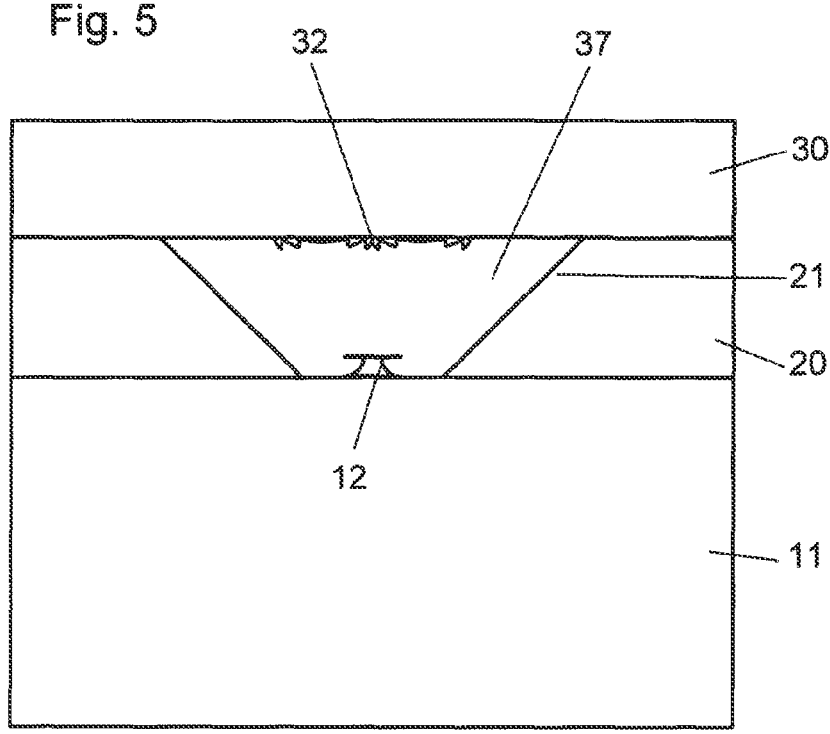
FIG. 5 shows a cross-section through a micro-optical element with a cover which is provided with a lens for ring-shaped focusing of the pumping beam (not illustrated)

According to FIG. 5, integrated into the cover (30) of a further embodiment of the micro-optical element (10) is an annular lens (32), preferably an annular Fresnel lens for ring-shaped focusing of the pumping beam onto the rotationally symmetrical body (14) of the microresonator (12). The pumping beam (not shown in FIG. 5) is focused by the annular lens (32) exclusively onto a narrow ring along the periphery of the rotationally symmetrical body (14). As compared with FIG. 2, the optical pumping of the rotationally symmetrical body (14) is more efficient and the threshold for the emission of coherent radiation can therefore be further lowered.

Figure 6:
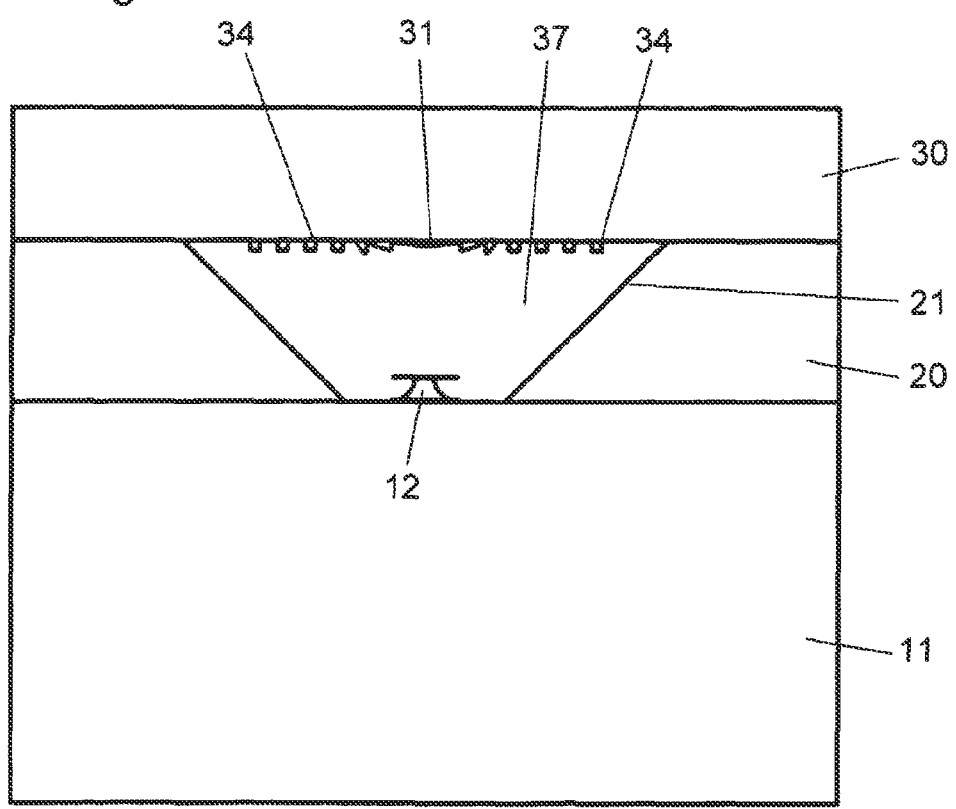
FIG. 6 shows a cross-section through a micro-optical element with a cover which is provided with a grating coupler for coupling the emitted light from the microresonator into the structure of the cover, and with a lens for point focusing of the pumping beam (not illustrated)

FIG. 6 shows a further embodiment of the micro-optical element (10) in which, in addition to a Fresnel lens (31) for point focusing of the pumping beam onto the structure of the rotationally symmetrical body (14) of the microresonator (12), a grating coupler (34) is introduced into the cover (30) as a diffractive structure for coupling-in the emission light reflected by the ring-shaped mirror (20). The cover (30) functions as a waveguide and guides the coupled-in emission light to a detector mounted laterally. By suitable configuration of the grating period, selective filtration of the pumping light can be achieved merely by the structure of the grating coupler (34). The pumping light is scattered by the grating coupler and is not fully coupled into the structure of the cover. The structure of the grating coupler (34) was also introduced onto the cover (30) by hot stamping, injection moulding or compression injection moulding. Alternatively, it can be applied by thermal bonding or gluing onto the structure of the cover (30).

In an alternative embodiment (not shown), the grating coupler is configured to couple out the pumping light (61) from the structure of the cover (30) onto the rotationally symmetrical body (14) of the microresonator (12). In this variant, the grating coupler is arranged above the structure of the microresonator (12) in the centre of the ring-shaped mirror (20). The cover (30) also functions as an optical waveguide in this case and guides the pumping light (61) which is coupled laterally into the cover (30) to the grating coupler.

The components shown in FIGS. 2 to 6 were also combined with one another in another manner, in particular so as simultaneously to pump the microresonator (12) efficiently by means of the pumping beam, to read out the emission light obtained from the microresonator (12) and to convey an analyte in a targeted manner via the fluidic inlet (35) and the fluidic channel (36) into the fluid chamber (37).

Figure 7:
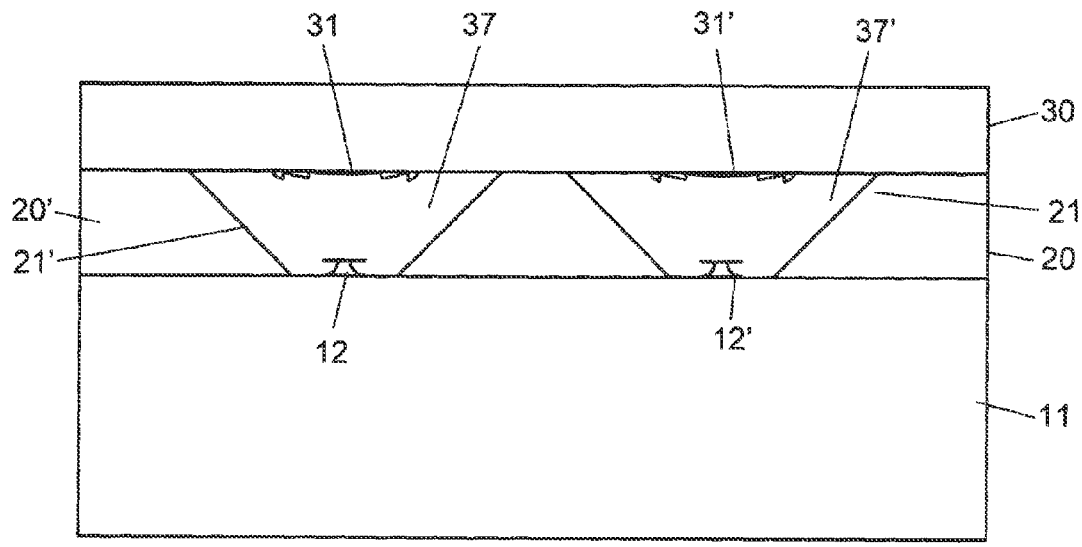
FIG. 7 shows a cross-section through a micro-optical array with two microresonators and a cover.

FIG. 7 shows a cross-section through a micro-optical array (40) according to the invention. Two microresonators (12, 12') are mounted on a resonator substrate (11). The functionalising of the two microresonators (12, 12') was carried out by dip-pen nanolithography. In the same array (40), the two microresonators (12, 12') were functionalised in different ways so that different substances from the analyte could be detected. The two microresonators (12, 12') are each surrounded by a light-reflecting ring-shaped mirror (20, 20'), wherein the respective shapes of the two light-reflecting ring-shaped mirrors (20, 20') are configured such that the light radiated from each of the two microresonators (12, 12') can be guided away from each of the microresonators (12, 12') as effectively as possible.

For this purpose, a suitable array of ring-shaped mirrors (20, 20') was structured by hot stamping at a distance from the microresonators (12, 12'). As the reflecting layer, a thin reflective layer (21, 21') of silver was vapour deposited onto the conical surface of the ring-shaped mirrors (20, 20'). For protection against oxidation, the silver layer was encapsulated by an $MgF_2$ layer. The resonator substrate (11) and the ring-shaped mirrors (20, 20') are adjusted to one another such that the microresonators (12, 12') are each situated in the centre of the respective ring-shaped mirrors (20, 20').

Integrated into the structure of the cover (30) are two Fresnel lenses (31, 31') for point focusing of the pumping beam (61) onto the rotationally symmetrical bodies (14, 14') of the microresonators (12, 12'). The distance between the two Fresnel lenses (31, 31') corresponds to the spacing of the microresonators (12, 12').

Figure 8:
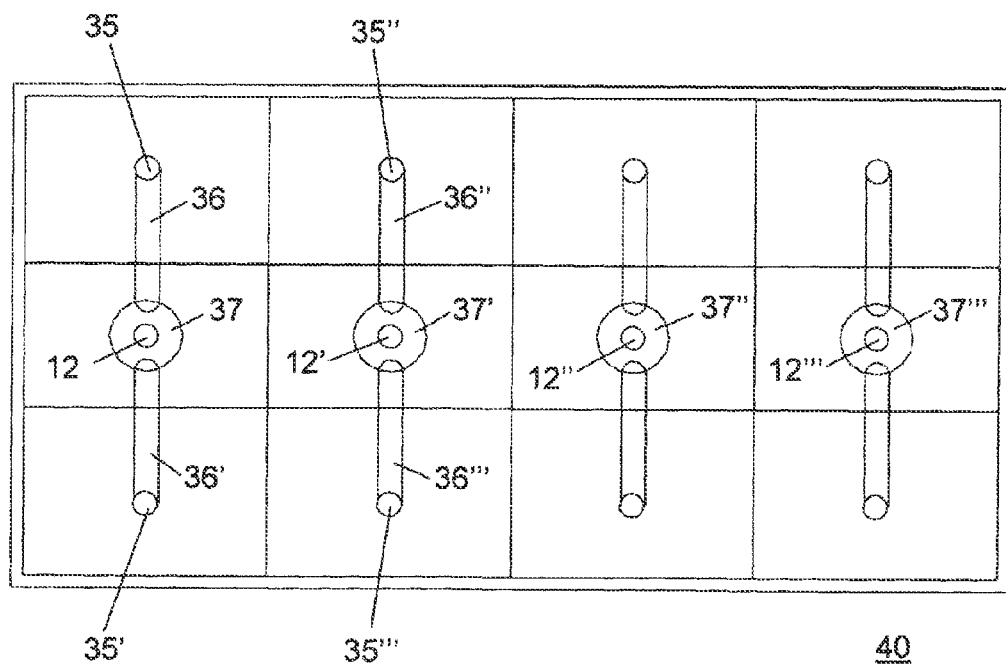
FIG. 8 shows a plan view of a micro-optical array with four microresonators and a fluidic structure introduced into the cover.

FIG. 8 shows a plan view of a further embodiment of the micro-optical array (40). Four microresonators (12, 12', 12", 12''') are mounted on a resonator substrate (11), each situated in the centre of the respective ring-shaped mirrors (20, 20', 20", 20'''). The analyte was conveyed via fluidic inlets (35, 35', ...) and fluidic channels (36, 36', ...) integrated in the cover (30) of the array (40) into the fluid chambers (37, 37', ...) to the microresonators (12, 12', ...). The fluidic structures were manufactured by means of hot stamping. The four different microresonators (12, 12', 12", 12''') of the array (40)

can be individually addressed fluidically via the fluidic inlets (35, 35', . . . ) and fluidic channels (36, 36', . . . ). The different functionalisations of the four microresonators (12, 12', 12", 12''') enabled selective detection of four different substances in the analyte.

Figure 9:
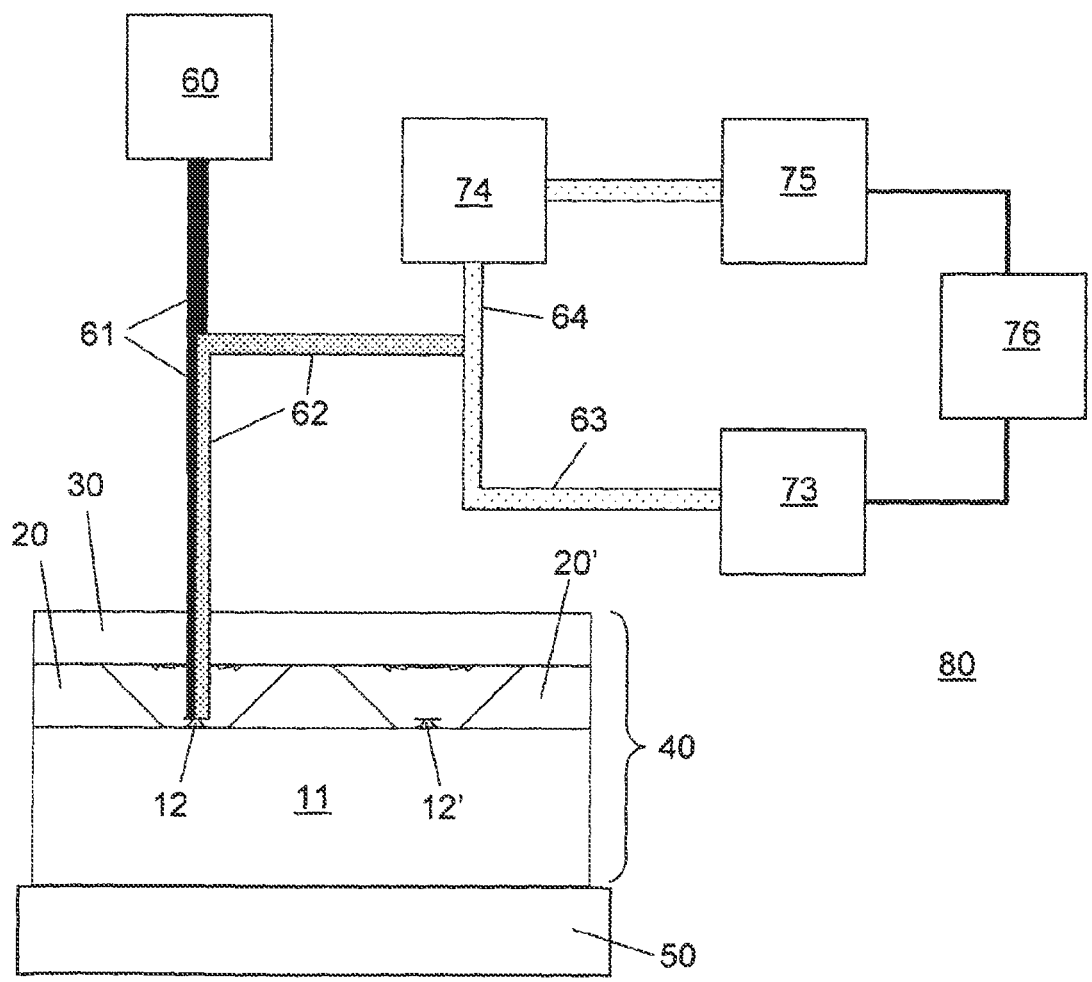
FIG. 9 shows a functional diagram of an optical sensor system.

In FIG. 9, a preferred optical sensor system (80) is shown which contains at least one micro-optical element (10) according to the invention or at least one micro-optical array (40) according to the invention. In order to excite the laser emission, the individual microresonators (12, 12' . . . ) of the micro-optical element (10) or of the micro-optical array (40) were pumped with a pulsed, diode-pumped Nd:YLF solid state laser (60) having a wavelength of 523 nm. In order to increase the efficiency of the laser excitation, integrated into the cover (30) over each microresonator (12, 12' . . . ) was a lens structure which focuses the pumping beam (61) onto the rotationally symmetrical body of the microresonators (12, 12' . . . ). The structuring of the lenses was achieved by hot stamping into a cyclic olefin copolymer (COC).

In order to compensate for thermally induced drift in the laser emission (62) of the microresonators (12, 12'), a temperature-regulated Peltier element was mounted under the resonator substrate (11) as a temperature stabilising device (50).

With a filter, in this case a longpass filter, the emission spectrum (62) of the microresonator (12) was separated from the pumping light (61). The filtered light was split into a reference beam (63) and a sensor beam (64). The intensity of the reference beam (63) was measured with a first photodiode as the reference diode (73), in order to correct variations or drift in the intensity (62) emitted by the microresonator (12, 12').

The sensor beam (64) was guided through a tunable filter (74) having a steep cut-off. A rotatably mounted, tunable thin-film filter was used as the tunable filter (74). It was possible to vary the filter characteristics by changing the incidence angle of the sensor beam (64) onto the tunable filter (74). The signal of a second photodiode as a measuring diode (75) connected downstream was compared with the signal of the reference diode (74). Evaluation of the measurement signals was carried out via evaluating electronics (76) or via software.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

The invention claimed is:

1. A micro-optical element comprising:
    a resonator substrate;
    at least one active optical microresonator including a rotationally symmetrical body and being disposed on the resonator substrate;
    a light-reflecting ring-shaped mirror that surrounds the rotationally symmetrical body such that the rotationally symmetrical body does not touch the light-reflecting ring-shaped mirror; and
    an at least partially optically transparent cover through which light emitted least one active optical microresonator can be guided,
    wherein the resonator substrate, the light-reflecting ring-shaped mirror, and the at least partially optically transparent cover are disposed so as to form a fluid chamber around the at least one active optical microresonator.

2. The micro-optical element of claim 1, wherein an angle profile of the light-reflecting ring-shaped mirror is matched to the emission profile of the rotationally symmetrical body such that light emitted by the at least one active optical microresonator can be reflected by the light-reflecting ring-shaped mirror at least one of: perpendicular to the resonator substrate or almost perpendicular to the resonator substrate.

3. The micro-optical element of claim 1, further comprising, disposed on or integrated into the at least partially optically transparent cover, at least one of: a lens configured for point focusing of a light beam, a lens configured for ring-shaped focusing of a light beam, or a grating coupler.

4. The micro-optical element of claim 1,
    wherein the at least partially optically transparent cover comprises one or more fluidic inlets and one or more fluidic channels.

5. The micro-optical element of claim 1, wherein a surface of the at least one active optical microresonator is provided with a functionalization configured to allow only certain molecules to attach to the microresonator.

6. A micro-optical array comprising:
    at least one resonator substrate; and
    at least two array elements disposed on the substrate, each array element including:
    one or more active optical microresonators, each having a rotationally symmetrical body;
    one or more light-reflecting ring-shaped mirrors surrounding the rotationally symmetrical body; and
    an at least partially optically transparent cover through which light emitted by the one or more active optical microresonators can be guided,
    wherein the resonator substrate, each of the one or more light-reflecting ring-shaped mirrors, and the at least partially optically transparent cover are disposed so as to form one or more fluid chambers around each of the one or more active optical microresonators.

7. The micro-optical array of claim 6, wherein an angle profile of each of the one or more light-reflecting ring-shaped mirrors is matched to the emission profile of a corresponding rotationally symmetrical body such that light emitted by a corresponding active optical microresonator can be reflected by the ring-shaped mirror at least one of: perpendicular to the resonator substrate and almost perpendicular to the resonator substrate.

8. The micro-optical array of claim 6, further comprising, disposed on or integrated into the at least partially optically transparent cover, at least one of: a lens configured for point focusing of a light beam, a lens configured for ring-shaped focusing of a light beam, or a grating coupler.

9. The micro-optical array of claim 6,
wherein the at least partially optically transparent cover comprises one or more fluidic inlets and one or more fluidic channels.

10. The micro-optical array of claim 6, wherein a surface of each of the one or more active optical microresonators is provided with a functionalization configured to allow only certain molecules to attach to the microresonator.

11. An optical sensor system comprising:
a device configured to excite the emission of light from at least one microresonator;
a micro-optical element including:
a resonator substrate,
at least one microresonator having a rotationally symmetrical body and being disposed on the resonator substrate, and
a light-reflecting ring-shaped mirror that surrounds the rotationally symmetrical body such that the rotationally symmetrically body does not touch the ring-shaped mirror;
an at least partially optically transparent cover including one or more fluidic inlets and one or more fluidic channels configured to feed an analyte to and remove an analyte from the at least one microresonator; and
a detector circuit configured to detect a frequency shift in the light emitted by the at least one microresonator.

12. The optical sensor system of claim 11, further comprising a tunable filter having a steep cut-off, for converting the frequency shift into an intensity change.

* * * * *